United States Patent [19]

Bundy

[11] 4,171,327

[45] Oct. 16, 1979

[54] 2-DECARBOXY-2-ALKYLCARBONYL-PGF COMPOUNDS

[75] Inventor: Gordon L. Bundy, Portage, Mich.

[73] Assignee: The Upjohn Company, Kalamazoo, Mich.

[21] Appl. No.: 925,507

[22] Filed: Jul. 17, 1978

Related U.S. Application Data

[62] Division of Ser. No. 888,695, Mar. 21, 1978, Pat. No. 4,123,463.

[51] Int. Cl.$^2$ ............................................ C07C 177/00
[52] U.S. Cl. .............................. 260/586 R; 260/590 C
[58] Field of Search .................... 560/121; 260/586 R, 260/590 C

[56] References Cited

U.S. PATENT DOCUMENTS 3,935,435  4/1976  Hayashi et al. ...................... 260/240

*Primary Examiner*—Robert Gerstl
*Attorney, Agent, or Firm*—Robert A. Armitage

[57] ABSTRACT

The present invention provides novel prostaglandin analogs wherein the C-2 carboxyl is replaced by alkylcarbonyl, i.e., a C-2 ketone. These novel 2-decarboxy-2-alkylcarbonyl-PG-type compounds are disclosed as improved gastrointestinal cytoprotective agents, being devoid or substantially devoid of other prostaglandin-type effects (e.g., smooth muscle or cardiovascular).

55 Claims, No Drawings

2-DECARBOXY-2-ALKYLCARBONYL-PGF COMPOUNDS

The present application is a divisional application of Ser. No. 888,695, filed Mar. 21, 1978, now U.S. Pat. No. 4,123,463.

The present invention relates to prostaglandin analogs, for which the essential material constituting disclosure therefor is incorporated by reference here from U.S. Pat. No. 4,123,463.

I claim:

1. A prostaglandin analog of the formula

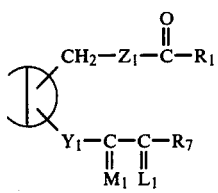

wherein  is

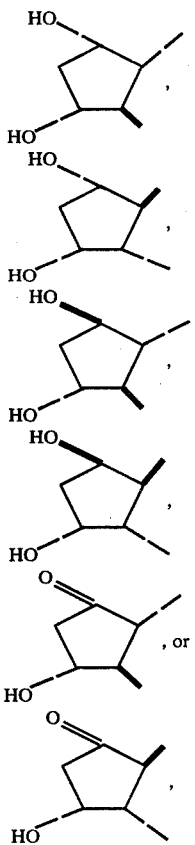

wherein $R_1$ is alkyl of one to 4 carbon atoms, inclusive;
wherein $L_1$ is

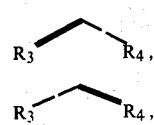

or a mixture of

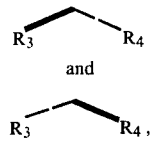

and

wherein $R_3$ and $R_4$ are hydrogen, methyl, or fluoro, being the same or different, with the proviso that one of $R_3$ and $R_4$ is methyl only when the other is hydrogen or methyl;
wherein $M_1$ is

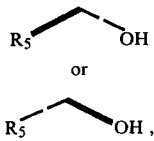

or

wherein $R_5$ is hydrogen or methyl;
wherein $R_7$ is
(1) $-(CH_2)_m-CH_3$,

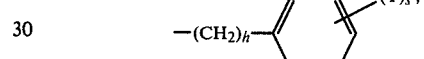

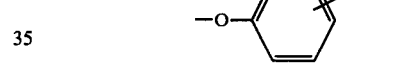

wherein h is zero to three, inclusive;
wherein m is one to 5, inclusive, s is zero, one, 2, or 3 and T is chloro, fluoro, trifluoromethyl, alkyl of one to 3 carbon atoms or alkoxy of one to 3 carbon atoms, the various T's being the same or different, with the proviso that not more than two T's are other than alkyl;
wherein $Y_1$ is
(1) trans—$CH=CH$—,
(2) cis—$CH=CH$—,
(3) —$CH_2CH_2$—, or
(4) —$C\equiv C$—; and
wherein $Z_1$ is
(1) cis—$CH=CH-CH_2-(CH_2)_g-CH_2$—,
(2) cis—$CH=CH-CH_2-(CH_2)_g-CF_2$—,
(3) cis—$CH_2-CH=CH-(CH_2)_g-CH_2$—,
(4) —$(CH_2)_3-(CH_2)_g-CH_2$—,
(5) —$(CH_2)_3-(CH_2)_g-CF_2$—,
(6) —$CH_2-O-CH_2-(CH_2)_g-CH_2$—,
(7) —$(CH_2)_2-O-(CH_2)_g-CH_2$—,
(8) —$(CH_2)_3-O-(CH_2)_g$—,
(9) —$C\equiv C-CH_2-(CH_2)_g-CH_2$—, or
(10) trans—$(CH_2)_2-(CH_2)_g-CH=CH$—,
wherein g is one, two, or three.

2. A prostaglandin analog according to claim 1, wherein $R_1$ is methyl.

3. A prostaglandin analog according to claim 2, wherein  is

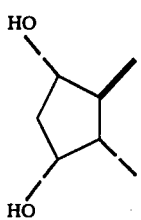

4. 2-Decarboxy-2-methylcarbonyl-8β,12α-PGF₂α, a prostaglandin analog according to claim 3.

5. A prostaglandin analog according to claim 2, wherein D is

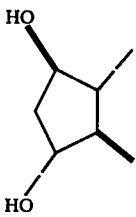

6. 2-Decarboxy-2-methylcarbonyl-PGF₂β, a prostaglandin analog according to claim 5.

7. A prostaglandin analog according to claim 2, wherein D is

8. 2-Decarboxy-2-methylcarbonyl-8β,12α-PGF₂β, a prostaglandin analog according to claim 7.

9. A prostaglandin analog according to claim 2, wherein D is

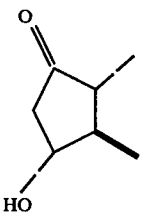

10. 2-Decarboxy-2-methylcarbonyl-PGE₂, a prostaglandin analog according to claim 9.

11. A prostaglandin analog according to claim 2, wherein D is

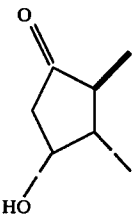

12. 2-Decarboxy-2-methylcarbonyl-8β,12α-PGE₂, a prostaglandin analog according to claim 10.

13. A prostaglandin analog according to claim 2, wherein D is

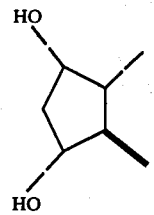

14. A prostaglandin analog according to claim 13, wherein $Y_1$ is cis—CH=CH—.

15. 2-Decarboxy-2-methylcarbonyl-13-cis-PGF₂α, a prostaglandin analog according to claim 14.

16. A prostaglandin analag according to claim 13, wherein $Y_1$ is —CH₂CH₂—.

17. 2-Decarboxy-2-methylcarbonyl-13,14-dihydro-PGF₂α, a prostaglandin analog according to claim 16.

18. A prostaglandin analog according to claim 13, wherein $Y_1$ is —C≡C—.

19. 2-Decarboxy-2-methylcarbonyl-13,14-didehydro-PGF₂α, a prostaglandin analog according to claim 18.

20. A prostaglandin analog according to claim 13, wherein $Y_1$ is trans—CH=CH—.

21. A prostaglandin analog according to claim 20, wherein $R_7$ is

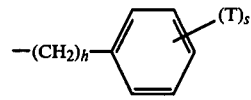

22. 2-Decarboxy-2-methylcarbonyl-17-phenyl-18,19,20-trinor-PGF₂α, a prostaglandin analog according to claim 21.

23. A prostaglandin analog according to claim 20, wherein $R_7$ is

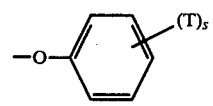

24. 2-Decarboxy-2-methylcarbonyl-16-phenoxy-17,18,19,20-tetranor-PGF₂α, a prostaglandin analog according to claim 23.

25. A prostaglandin analog according to claim 20, wherein $R_7$ is —(CH₂)$_m$—CH₃—.

26. A prostaglandin analog according to claim 25, wherein $Z_1$ is cis—CH=CH—CH₂—(CH₂)$_g$—CF₂—.

27. 2-Decarboxy-2-methylcarbonyl-2,2-difluoro-PGF₂α, a prostaglandin analog according to claim 26.

28. A prostaglandin analog according to claim 25, wherein $Z_1$ is cis—CH₂—CH=CH—(CH₂)$_g$—CH₂—.

29. 2-Dicarboxy-2-methylcarbonyl-cis-4,5-didehydro-16,16-dimethyl-PGF₁α, a prostaglandin analog according to claim 28.

30. A prostaglandin analog according to claim 25, wherein $Z_1$ is —(CH₂)₃—(CH₂)$_g$—CH₂—.

31. 2-Decarboxy-2-methylcarbonyl-PGF₁α, a prostaglandin analog according to claim 30.

32. A prostaglandin analog according to claim 25, wherein $Z_1$ is $-(CH_2)_3-(CH_2)_g-CF_2-$.

33. 2-Decarboxy-2-methylcarbonyl-2,2-difluoro-PGF$_1\alpha$, a prostaglandin analog according to claim 32.

34. A prostaglandin analog according to claim 25, wherein $Z_1$ is $-CH_2-O-CH_2-(CH_2)_g-CH_2-$.

35. 2-Decarboxy-2-methylcarbonyl-5-oxa-PGF$_1\alpha$, a prostaglandin analog according to claim 34.

36. A prostaglandin analog according to claim 25, wherein $Z_1$ is $-(CH_2)_2-O-(CH_2)_g-CH_2-$.

37. 2-Decarboxy-2-methylcarbonyl-4-oxa-PGF$_1\alpha$, a prostaglandin analog according to claim 36.

38. A prostaglandin analog according to claim 25, wherein $Z_1$ is $-(CH_2)_3-O-(CH_2)_g-$.

39. 2-Decarboxy-2-methylcarbonyl-3-oxa-PGF$_1\alpha$, a prostaglandin analog according to claim 38.

40. A prostaglandin analog according to claim 25, wherein $Z_1$ is $-C\equiv C-CH_2-(CH_2)_g-CH_2-$.

41. 2-Decarboxy-2-methylcarbonyl-5,6-didehydro-PGF$_2\alpha$, a prostaglandin analog according to claim 40.

42. A prostaglandin analog according to claim 25, wherein $Z_1$ is $-CH_2-C\equiv C-(CH_2)_g-CH_2-$.

43. 2-Decarboxy-2-methylcarbonyl-4,4,5,5-tetradehydro-PGF$_1\alpha$, a prostaglandin analog according to claim 42.

44. A prostaglandin analog according to claim 25, wherein $Z_1$ is trans-$(CH_2)_2-(CH_2)_g-CH=CH-$.

45. 2-Decarboxy-2-methylcarbonyl-trans-2,3-didehydro-PGF$_1\alpha$, a prostaglandin analog according to claim 44.

46. A prostaglandin analog according to claim 25, wherein $Z_1$ is cis-$CH=CH-CH_2-(CH_2)_g-CH_2-$.

47. A prostaglandin analog according to claim 46, wherein $R_5$ is methyl.

48. 2-Decarboxy-2-methylcarbonyl-15-methyl-PGF$_2\alpha$, a prostaglandin analog according to claim 46.

49. A prostaglandin analog according to claim 46, wherein $R_5$ is hydrogen.

50. A prostaglandin analog according to claim 46, wherein one of $R_3$ and $R_4$ is fluoro.

51. 2-Decarboxy-2-methylcarbonyl-16,16-difluoro-PGF$_2\alpha$, a prostaglandin analog according to claim 50.

52. A prostaglandin analog according to claim 49, wherein at least one of $R_3$ and $R_4$ is methyl.

53. 2-Decarboxy-2-methylcarbonyl-16,16-dimethyl-PGF$_2\alpha$, a prostaglandin analog according to claim 52.

54. A prostaglandin analog according to claim 49, wherein $R_3$ and $R_4$ are both hydrogen.

55. 2-Decarboxy-2-methylcarbonyl-PGF$_2\alpha$, a prostaglandin analog according to claim 54.

* * * * *